ns patents are examiner
United States Patent [19]
Koulbanis et al.

[11] 4,324,802
[45] Apr. 13, 1982

[54] COSMETIC OIL AND COMPOSITION CONTAINING THE SAME

[75] Inventors: Constantin Koulbanis; Catherine Millet; Arlette Zabotto, all of Paris; Alain Brun, Pavillons-sous-Bois, all of France

[73] Assignee: L'Oreal, Paris, France

[21] Appl. No.: 211,946

[22] Filed: Dec. 1, 1980

[30] Foreign Application Priority Data

Dec. 18, 1979 [FR] France ................................ 79 30956
Aug. 13, 1980 [FR] France ................................ 80 17899

[51] Int. Cl.³ .......................... A61K 7/48; A61K 7/44; A61K 7/26; A61K 7/021
[52] U.S. Cl. ........................................ 424/364; 424/60; 424/61; 424/63; 424/64; 424/195
[58] Field of Search ...................... 424/195, 61, 60, 63, 424/64, 364

[56] References Cited
FOREIGN PATENT DOCUMENTS
50-58241  5/1975  Japan .................................. 424/364

*Primary Examiner*—Donald B. Moyer

[57] ABSTRACT

A cosmetic oil comprises a mixture of at least jojoba oil, turnsole oil and a non-saponifiable fraction.

12 Claims, No Drawings

COSMETIC OIL AND COMPOSITION CONTAINING THE SAME

The present invention relates to a new cosmetic oil and to cosmetic compositions containing the same.

It is known that cosmetic oils are liquid products and exhibit little volatility at ambient temperature. These oils are generally employed to dissolve various water-insoluble organic substances whose presence is desirable in cosmetic compositions.

Further, these cosmetic oils are water-insoluble and can provide emulsions in which water constitutes either the continuous phase, or the dispersed phase in the form of fine droplets.

Such cosmetic oils are characterized principally by an unctuous feel or touch, by their lubricating properties which generally facilitate their use and by their spreadability onto the skin so as to leave on the surface thereof a hydrophobic film.

This latter property also includes the emollient character of cosmetic oils. This emollient activity of the oil is expressed by an improvement or the maintenance of the suppleness of the skin which can be explained by the formation of this hydrophobic film which maintains an appropriate amount of water associated with the skin by preventing its evaporation even under cold or dry atmospheric conditions. Moreover, in the case of cosmetic compositions in emulsion form, this emollient activity can be explained in part by the ability of the emulsion used to supply water thereby maintaining the appropriate amount of water of the skin.

However, it is well known that all oils do not have the same degree of emollient activity and that only certain ones are useful in cosmetic products.

On the other hand, as has been noted above, the oily touch or feel of the oil which is one of the results of its lubricating properties, constitutes an interesting property since it facilitates the application of the oil onto the skin.

However, this characteristic can be a disadvantage in the case where the film which remains on the skin after application thereto of the cosmetic composition, retains this oily feel, or, at times, a slightly adhesive or sticky feel or touch which is considered disagreeable and undesirable.

Such a disadvantage is practically always encountered although to varying degrees, with most known cosmetic oils.

Moreover, tests have shown that certain oils are difficult to spread onto the skin. These oils create during the spreading a "pulling" sensation which is considered disagreeable.

Another disadvantage often experienced in the use of oils in cosmetic compositions, is that the oily film deposited on the skin has a more or less accentuated shiny appearance which is generally considered unaesthetic.

The present invention thus relates to a cosmetic oil which does not exhibit, or which exhibits only to a small degree, these various disadvantages.

Oils which are used in cosmetic products are principally oils of vegetable origin. It is known that vegetable oils contain, in a major part, saponifiable esters, principally fatty acid glycerides and also a non-saponifiable fraction.

It is also known that the non-saponifiables have some very interesting dermatological properties and their use in cosmetic compositions has been recommended principally to improve the appearance of aging, dry or wrinkled skin.

However, compositions containing non-saponifiable fractions exhibit, as do essentially all compositions containing oils, those disadvantages which have been noted above, and principally, the deposit on the skin of an oily film which is disagreeable to the touch and shiny.

Generally it is considered that the more an oil leaves an oily film having a disagreeable appearance and feel on the skin, the less is its penetrating power.

The present invention on the other hand relates to a cosmetic oil which exhibits improved penetrating power.

This cosmetic oil of the present invention contains a mixture of at least two vegetable oils, the said vegetable oils being at least jojoba oil and turnsole oil, and at least one previously extracted non-saponifiable fraction.

Representative non-saponifiable fractions include principally, the non-saponifiables of soybean, avocado, corn and turnsole, and mixtures thereof. The non-saponifiable fractions can be prepared in accordance with known procedures, such as by submitting the fatty body to saponification and/or to an extraction operation of the non-saponifiable portion.

It is also known that the non-saponifiable fractions include a large number of components, and their composition is generally not entirely known. Obviously, the composition of a non-saponifiable fraction can depend principally on the process employed to prepare it, and in particular on the extraction solvents used.

Moreover, the non-saponifiable fractions obtained and employed in the present invention can also contain a certain amount of saponifiable components and thus constitute a fraction enriched in non-saponifiable products.

The expression "non-saponifiable fraction" as used in the context of the present invention is intended to include not only a previously extracted non-saponifiable fraction (or a portion thereof), but also a fraction enriched in non-saponifiables which also contains a portion of the saponifiable components of the starting oil. The amount of non-saponifiable components in such an enriched fraction is greater than 40 weight percent.

The novel cosmetic oil of the invention contains, generally, by weight, from 20 to 40 percent of a non-saponifiable fraction, from 20 to 45 percent of jojoba oil and from 25 to 40 percent of turnsole oil.

When the non-saponifiable fraction is provided in the form of a mixture of two non-saponifiables, for example, soybean non-saponifiables and avocado non-saponifiables, the weight ratio between these two non-saponifiables can vary between ¼ and 3/1, respectively, and is preferably 2/1.

A cosmetic composition containing the cosmetic oil of the present invention as defined above is also an object of the present invention. Other components included in such compositions can be conventional materials.

The cosmetic composition of the present invention generally is one containing an oil and is preferably one for application to the skin to improve the appearance thereof. The general type of such compositions, components other than the novel cosmetic oil of this invention which are included therein, and their preparation and use, are well known to the skilled artisan. Generally, such compositions contain at least 10% of the cosmetic oil of the present invention.

Representative cosmetic compositions of the present invention include those which are provided in the form of a fluid emulsion, such as a milk, a lotion or a more thick emulsion, such as a cream.

These cosmetic compositions are, more particularly, emollient milks or creams, milks or creams for the care of the hands, makeup remover creams or milks, complexion foundations, sunscreen milks or creams, artificial tanning milks or creams, anti-perspiration milks or creams, shaving creams or foams, pre-shave lotions or even milks or creams for the care of baby skin.

The cosmetic oil of the present invention can also be included in the preparation of other compositions such as, principally, lipsticks to impart color to the lips (lip rouge) or to avoid chapping, eye makeup compositions and face makeup compositions.

The cosmetic compositions of the present application which are provided in the form of solutions are principally sunscreen oils which contain in addition to the cosmetic oil a sunscreen which absorbs ultraviolet light, oils for the hands, oils for the body, pre-shave or after shave oils or bath oils and the like.

Generally, in these solution-type compositions, the amount of the cosmetic oil of the present invention ranges from 10–100%; in other cosmetic compositions of the present invention, this cosmetic oil is generally present in an amount ranging from 10 to 50 weight percent, relative to the total weight of the composition.

The cosmetic compositions of the present invention generally contain, in addition to the cosmetic oil, at least one of the following components: a preservative agent, an anti-oxidant agent, a perfume, a dye agent or the like.

To evidence the improved penetrating power of the cosmetic oil of the present invention, the following test has been effected.

There is applied to the skin of the back of the hand of volunteers the same amount of one of the following oils:

Oil No. 1—jojoba oil
Oil No. 2—turnsole oil
Oil No. 3—non-saponifiables (⅓ avocado non-saponifiables +⅔ soybean non-saponifiables)
Oil No. 4—50:50 mixture of jojoba oil and turnsole oil
Oil No. 5—50:50 mixture of jojoba oil and the non-saponifiables defined in No. 3
Oil No. 6—50:50 mixture of turnsole oil and the non-saponifiables defined in No. 3
Oil No. 7—1:1:1 mixture of jojoba oil, turnsole oil and the non-saponifiables defined in No. 3

Each oil has been applied to the hands of eight users who have noted on a scale ranging from 0 to 10, the penetrating power of the oil applied. The penetrating power is estimated according to the following criteria: the feel after application; the appearance after application; and the speed of penetration.

Each oil has been ranked by the testers using the scale of 0 to 10, the value 10 corresponding to a very good penetrating power.

The average values obtained are as follows:

| Oil No. | Average Value Obtained |
| --- | --- |
| 1 | 5.81 |
| 2 | 4.69 |
| 3 | 6.13 |
| 4 | 6.19 |
| 5 | 7.81 |
| 6 | 5.50 |
| 7 | 8.31 |

This test shows that Oil No. 7 exhibits significantly improved penetrating power compared to the other oils tested.

The following non-limiting examples illustrate the present invention.

EXAMPLES OF PREPARING THE COSMETIC OILS

|  | % by Weight |
| --- | --- |
| Example A |  |
| Jojoba oil | 33.3 |
| Turnsole oil | 33.3 |
| Soybean non-saponifiables | 22.2 |
| Avocado non-saponifiables | 11.2 |
| Example B |  |
| Jojoba oil | 35 |
| Turnsole | 40 |
| Avocado non-saponifiables | 25 |
| Example C |  |
| Jojoba oil | 20 |
| Turnsole oil | 40 |
| Avocado non-saponifiables | 15 |
| Soybean non-saponifiables | 25 |
| Example D |  |
| Jojoba oil | 30 |
| Turnsole oil | 35 |
| Avocado non-saponifiables | 15 |
| Soybean non-saponifiables | 20 |
| Example E |  |
| Jojoba oil | 35 |
| Turnsole oil | 30 |
| Avocado non-saponifiables | 15 |
| Soybean non-saponifiables | 20 |
| Example F |  |
| Jojoba oil | 40 |
| Turnsole oil | 30 |
| Avocado non-saponifiables | 10 |
| Soybean non-saponifiables | 20 |
| Example G |  |
| Jojoba oil | 33.3 |
| Turnsole oil | 33.3 |
| Corn non-saponifiables | 17.0 |
| Turnsole non-saponifiables | 16.4 |
| Example H |  |
| Jojoba oil | 30 |
| Turnsole oil | 40 |
| Corn non-saponifiables | 30 |
| Example I |  |
| Jojoba oil | 45 |
| Turnsole oil | 30 |
| Turnsole non-saponifiables | 25 |
| Example J |  |
| Jojoba oil | 35 |
| Turnsole oil | 35 |
| Pistachio non-saponifiables | 10 |
| Avocado non-saponifiables | 20 |
| Example K |  |
| Jojoba oil | 25 |
| Turnsole oil | 25 |
| Avocado oil | 25 |
| Avocado non-saponifiables | 25 |

Preparation of Cosmetic Compositions

EXAMPLE 1

Oil for the body

|  | % by Wt. |
|---|---|
| Cosmetic oil of Example A | 99.8 |
| BHA (butylhydroxy anisole) | 0.1 |
| BHT (butylhydroxy toluene) | 0.1 |
|  | 100.0 |

A comparable body oil is produced by replacing the cosmetic oil of Example A by that of Example G.

Moreover, a sunscreen oil is formulated using this body oil by including therein a conventional ultraviolet absorbing sunscreen agent.

These body or sunscreen oils can also contain a perfume.

EXAMPLE 2

Sunscreen Oil

|  | % by Wt. |
|---|---|
| Cosmetic oil of Example A | 94.8 |
| BHA | 0.1 |
| BHT | 0.1 |
| Sunscreen agent sold under the tradename "Parsol-Ultra" | 5.0 |
|  | 100.0 |

This sunscreen oil can also contain a perfume.

In this Example the cosmetic oil of Example A can advantageously be replaced by the same amount of the cosmetic oil of Example G or H.

EXAMPLE 3

Makeup remover milk

|  | % by Wt. |
|---|---|
| Cosmetic oil of Example A | 15.0 |
| Glycerol stearate | 2.0 |
| Stearic acid | 1.4 |
| Triethanolamine | 1.3 |
| High molecular weight carboxy vinyl polymer, sold under the tradename "Carbopol 934" | 0.6 |
| Methyl parahydroxy benzoate | 0.25 |
| BHA | 0.10 |
| BHT | 0.10 |
| Perfume, sufficient amount | |
| Sterile demineralized water sufficient amount for | 100. |

A comparable makeup remover milk is prepared by replacing the cosmetic oil of Example A by that of Example G.

EXAMPLE 4

Body milk

|  | % by Wt. |
|---|---|
| Cosmetic oil of Example C | 15.00 |
| Mixture of alcohols and sterols of lanolin, sold under the tradename "Amerchol L101" | 0.30 |
| Stearic acid | 1.40 |
| Self-emulsifiable glycerol monostearte | 2.00 |
| Cetyl alcohol | 0.20 |
| Triethanolamine | 0.95 |
| High molecular weight carboxyvinyl polymer sold under the tradename "Carbopol 941" | 0.25 |
| Propyleneglycol | 2.00 |
| BHA | 0.10 |
| BHT | 0.10 |
| Methyl parahydroxybenzoate | 0.35 |
| Perfume, sufficient amount | |
| Water, sufficient amount for | 100 |

A comparable body milk is prepared by replacing the cosmetic oil of Example C by that of Example I.

EXAMPLE 5

Skin care cream

|  | % by Wt. |
|---|---|
| Self-emulsifiable glycerol monostearate | 5.0 |
| Cosmetic oil of Example F | 26.0 |
| Methyl parahydroxybenzoate | 0.3 |
| "Carbopol 940" | 0.4 |
| Triethanolamine | 0.4 |
| BHA | 0.1 |
| BHT | 0.1 |
| Perfume, sufficient amount | |
| Sterile demineralized water, sufficient amount for | 100 |

A comparable skin care cream is prepared by replacing the cosmetic oil of Example F by that of Example H.

EXAMPLE 6

Skin care cream

|  | % by Wt. |
|---|---|
| Magnesium lanolate | 2.85 |
| Lanolin alcohol | 6.65 |
| Cosmetic oil of Example J | 48.30 |
| Ozokerite | 2.00 |
| BHA | 0.10 |
| BHT | 0.10 |
| Methyl parahydroxybenzoate | 0.10 |
| Sterile demineralized water, sufficient for | 100 |

In this Example the cosmetic oil of Example J can advantageously be replaced by the same amount of the cosmetic oil of Example G, H or I.

EXAMPLE 7

Sunscreen cream

|  | % by Wt. |
|---|---|
| Self-emulsifiable glycerol monostearate | 5.0 |
| Cosmetic oil of Example H | 26.0 |
| Methyl-parahydroxybenzoate | 0.3 |
| "Carbopol 940" | 0.4 |
| Triethanolamine | 0.4 |
| BHA | 0.1 |
| BHT | 0.1 |
| Sunscreen agent, sold under the tradename "Parsol-Ultra" | 5.0 |
| Perfume, sufficient amount | |

-continued

| | % by Wt. |
|---|---|
| Sterile demineralized water, sufficient amount for | 100 |

In this Example the cosmetic oil of Example H can advantageously be replaced by the same amount of the cosmetic oil of Example D, G or I.

EXAMPLE 8

Sunscreen cream

| | % by Wt. |
|---|---|
| Magnesium lanolate | 2.85 |
| Lanolin alcohol | 6.65 |
| Cosmetic oil of Example E | 48.30 |
| Ozokerite | 2.00 |
| BHA | 0.10 |
| BHT | 0.10 |
| Sunscreen agent, sold under the tradename "Parasol-Ultra" | 5.00 |
| Methyl parahydroxybenzoate | 0.10 |
| Sterile demineralized water, sufficient amount for | 100 |

In this Example the cosmetic oil of Example E can advantageously be replaced by the same amount of the cosmetic oil of Example B, H or I.

EXAMPLE 9

Complexion foundation

| | $ by Wt. |
|---|---|
| Isopropyl lanolate | 4.0 |
| Stearic acid | 2.6 |
| Self-emulsifiable glycol stearate | 5.0 |
| Cosmetic oil of Example K | 20.0 |
| Triethanolamine | 1.2 |
| Sodium lauryl sulfate | 1.1 |
| Bentonite | 2.5 |
| BHA | 0.1 |
| BHT | 0.1 |
| Methyl parahydroxybenzoate, sufficient amount | |
| Perfume, sufficient amount | |
| Demineralized water, sufficient amount for | 100 |

In addition

Titanium oxide, iron oxide and talc, each in a sufficient amount according to the desired color and covering power.

In this Example, the cosmetic oil of Example K can be replaced by that of Example G.

What is claimed is:

1. A cosmetic oil for improving or maintaining the suppleness of the skin and being spreadable on the skin so as to leave thereon a hydrophobic film having a non-oily, unctuous feel or touch comprising a mixture of from 20 to 45 weight percent jojoba oil, 25 to 40 weight percent turnsole oil and 20 to 40 weight percent of a previously extracted non-saponifiable fraction of a vegetable oil selected from the group consisting of soybean oil, avocado oil, corn oil, turnsole oil and mixtures thereof.

2. The cosmetic oil of claim 1 wherein said non-saponifiable fraction of said vegetable oil is a fraction enriched in non-saponifiables wherein the amount of said non-saponifiables is greater than 40 weight percent thereof.

3. The cosmetic oil of claim 1 wherein said non-saponifiable fraction is a mixture of soybean oil non-saponifiables and avocado oil non-saponifiables wherein the weight ratio of soybean oil non-saponifiables to avocado oil non-saponifiables ranges from 1:4 to 3:1, respectively.

4. The cosmetic oil of claim 3 wherein the weight ratio of soybean oil non-saponifiables to avocado oil non-saponifiables is 2:1, respectively.

5. A method for improving and maintaining the suppleness of the skin comprising applying thereto an effective amount of the cosmetic oil of claim 3.

6. A method for improving and maintaining the suppleness of the skin comprising applying thereto an effective amount of the cosmetic oil of claim 1.

7. A cosmetic oil for improving or maintaining the suppleness of the skin and being spreadable on the skin so as to leave thereon a hydrophobic film having a non-oily, unctuous feel or touch consisting essentially of a 1:1:1 mixture by weight of jojoba oil:turnsole oil:mixture of ⅓ non-saponifiables of avocado oil and ⅔ non-saponifiables of soybean oil.

8. A method for improving and maintaining the suppleness of the skin comprising applying thereto an effective amount of the cosmetic oil of claim 7.

9. In a cosmetic composition for application to the skin containing a cosmetic oil to improve or maintain the suppleness of the skin, said cosmetic oil being spreadable on the skin so as to leave thereon a hydrophobic film having a non-oily, unctuous feel or touch, the improvement comprising as the cosmetic oil an effective amount of a mixture of from 20 to 45 weight percent jojoba oil, 25 to 40 weight percent turnsole oil and 20 to 40 weight percent of a previously extracted non-saponifiable fraction of a vegetable oil selected from the group consisting of soybean oil, avocado oil, corn oil, turnsole oil and mixtures thereof.

10. The cosmetic composition of claim 9 wherein said cosmetic oil is present in an amount of at least 10 weight percent based on the total weight of said cosmetic composition.

11. The cosmetic composition of claim 9 wherein said cosmetic oil is present in an amount ranging from 10 to 50 weight percent based on the total weight of said composition.

12. The cosmetic composition of claim 9 wherein said cosmetic oil is present in an amount ranging from 10 to 100 weight percent based on the total weight of said composition.

* * * * *